(12) United States Patent
Viellerobe et al.

(10) Patent No.: US 10,875,322 B2
(45) Date of Patent: Dec. 29, 2020

(54) DEVICE AND METHOD FOR THE DEPOSITION OF PARTICLES ON A TARGET

(71) Applicants: Universite de Bordeaux, Bordeaux (FR); Institut National de la Santé et de la Recherche Médicale (INSERM), Paris (FR)

(72) Inventors: Bertrand Viellerobe, Merignac (FR); Romain Vaucelle, Bordeaux (FR); Fabien Guillemot, Preignac (FR)

(73) Assignees: Universite de Bordeaux, Bordeaux (FR); Institut National de la Santé et de la Recherche Médicale (INSERM), Paris (FR)

( * ) Notice: Subject to any disclaimer, the term of this patent is extended or adjusted under 35 U.S.C. 154(b) by 0 days.

(21) Appl. No.: 16/494,697

(22) PCT Filed: Mar. 8, 2018

(86) PCT No.: PCT/FR2018/050532
§ 371 (c)(1),
(2) Date: Sep. 16, 2019

(87) PCT Pub. No.: WO2018/167399
PCT Pub. Date: Sep. 20, 2018

(65) Prior Publication Data
US 2020/0009877 A1    Jan. 9, 2020

(30) Foreign Application Priority Data
Mar. 15, 2017 (FR) ..................................... 17 52128

(51) Int. Cl.
*B41J 2/44* (2006.01)
*B41J 2/45* (2006.01)
(Continued)

(52) U.S. Cl.
CPC ............... *B41J 2/442* (2013.01); *B41J 2/451* (2013.01); *C12M 21/08* (2013.01); *C12M 33/00* (2013.01);
(Continued)

(58) Field of Classification Search
CPC ........ B41J 2/442; B41J 2/451; B41J 2202/03; C12M 21/08; C12M 33/00; G02B 21/32;
(Continued)

(56) References Cited

U.S. PATENT DOCUMENTS

2015/0224291 A1* 8/2015 Guillemot .............. C12M 21/08
604/290

FOREIGN PATENT DOCUMENTS

WO   2003/050620 A1   6/2003
WO   2016/097619 A1   6/2016

OTHER PUBLICATIONS

Barron et al., Laser Printing: A Novel Technique for Creating Heterogeneous 3-Dimensional Cell Patterns, Biomed Micro Devices, vol. 6, No. 2, (Jun. 2004), pp. 139-147 (abstract only).
(Continued)

*Primary Examiner* — Bradley W Thies
(74) *Attorney, Agent, or Firm* — TraskBritt (57) ABSTRACT

A device for deposition of particles on a target from a transparent slide having a film formed by a fluid containing suspended particles, by locally exciting the film using a laser, includes means for observing the local excitation region. The observation means comprise a sensor and a light source, the optical axes of which are substantially shared in a space between an optical splitter and the film. The optical beam of the imaging system and the optical beam of the laser are coaxially arranged in the space between the controlled optical deflection means and the film. The device comprises a first focusing optical unit arranged between the controlled
(Continued)

optical deflection means and the film. The device comprises a second image-combining optical unit positioned between the sensor and the splitter, the sensor being positioned in the focal plane of the second optical unit.

20 Claims, 6 Drawing Sheets

(51) Int. Cl.
| | | |
|---|---|---|
| *C12M 3/00* | (2006.01) | |
| *C12M 1/26* | (2006.01) | |
| *G02B 21/32* | (2006.01) | |
| *G02B 27/10* | (2006.01) | |
| *B33Y 30/00* | (2015.01) | |
| *B33Y 70/00* | (2020.01) | |
| *B33Y 80/00* | (2015.01) | |

(52) U.S. Cl.
CPC ......... *G02B 21/32* (2013.01); *G02B 27/1073* (2013.01); *B33Y 30/00* (2014.12); *B33Y 70/00* (2014.12); *B33Y 80/00* (2014.12); *B41J 2202/03* (2013.01)

(58) Field of Classification Search
CPC .. G02B 27/1073; G02B 21/084; B33Y 30/00; B33Y 70/00; B33Y 80/00
See application file for complete search history.

(56) References Cited

OTHER PUBLICATIONS

Guillemot et al., High-Throughput Laser Printing of Cells and Biomaterials for Tissue Engineering, Acta Biomater, vol. 6, No. 7, (Jul. 2010), pp. 2494-2500 (abstract only).
Hopp et al., Laser-Induced Forward Transfer, Tissue Engineering, vol. 11, No. 11-12, (Jan. 13, 2006), (abstract only).
International Search Report for International Application No. PCT/FR2018/050532 dated May 28, 2018, 3 pages.
International Written Opinion for International Application No. PCT/FR2018/050532 dated May 28, 2018, 5 pages.
Riester et al., Laser Tool for Single Cell Transfer, Journal of Laser Micro/Nanoengineering, vol. 9, No. 2, (2014), pp. 93-97.

* cited by examiner

DEVICE AND METHOD FOR THE DEPOSITION OF PARTICLES ON A TARGET

CROSS-REFERENCE TO RELATED APPLICATIONS

This application is a national phase entry under 35 U.S.C. § 371 of International Patent Application PCT/FR2018/050532, filed Mar. 8, 2018, designating the United States of America and published as International Patent Publication WO 2018/167399 A1 on Sep. 20, 2018, which claims the benefit under Article 8 of the Patent Cooperation Treaty to French Patent Application Serial No. 1752128, filed Mar. 15, 2017.

TECHNICAL FIELD

The present disclosure concerns the field of laser bio-printing by a computer-assisted transfer process for modelling and assembling living and optionally non-living materials with a prescribed 2D or 3D organization in order to produce bioengineered structures for use in regenerative medicine, pharmacology and cell biology studies.

BACKGROUND

Laser-assisted bio-printing allows the high-precision organization of individual elements of the tissue during its manufacture via layer-by-layer deposition of cells and biomaterials. It enables reproduction of 3D tissue with a specific geometry. The "bottom-up" approach, based on assembling an object brick by brick and then layer by layer, is compatible with an automation of the tissue manufacturing process and can operate in a sterile environment. In addition, automation could reduce costs and improve the quality and reproducibility of biological tissue manufacturing.

The state of the art is a solution known as "AFA-LIFT" and described in the article by B. Hopp, T. Smausz, N. Kresz, N. Barna, Z. Bor, L. Kolozsvâri, D. B. Chrisey, A. Szabo, and A. Nôgrâdi, "Survival and proliferative ability of various living cell types after laser-induced forward transfer," Tissue Eng. 11, 1817-23 (2005).

The article by J. A. Barron, P. Wu, H. D. Ladouceur, and B. R. Ringeisen, "Biological laser printing: a novel technique for creating heterogeneous 3-dimensional cell patterns," Biomed. Microdevices 6, 139-147 (2004), also describes equipment of the "AFA LIFT or DRL-LIFT" type, where the laser direction is fixed, and the film supporting the cells to be transferred is mobile.

Another article, published in the "Journal of laser micro/nanoengineering," Vol. 9, No 2-2014 under the title "Laser tool for single cell transfer," describes another example of process and equipment of the AFA-LIFT type.

The article by F. Guillemot, A. Souquet, S. Catros, B. Guillotin, J. Lopez, M. Faucon, B. Pippenger, R. Bareille, M. Rémy, S. Bellance, P. Chabassier, J. C. Fricain, and J. Amédée, "High-throughput laser printing of cells and biomaterials for tissue engineering," Acta Biomater. 6, 2494-2500 (2010), describes an example of equipment to implement such a process.

Patent Application Publication No. WO2016097619 describes a method and equipment for printing with at least one ink, the method comprising a step of focusing a laser beam so as to generate a cavity in an ink film, a step of forming at least one ink droplet from a free surface of the ink film and a step of depositing the droplet onto a depositing surface of a receiving substrate, wherein the laser beam is oriented in the direction opposite to the gravitational force, the free surface of the film being oriented upward toward the depositing surface placed over the ink film.

This configuration makes it possible, in particular, to obtain a substantially constant thickness E for the ink film, while limiting the occurrence of settling phenomena. It also enables the use a wide range of inks.

The previously known solutions do not allow the transferable bioink film to be observed and the laser pulse to be triggered in the same sequence, i.e., simultaneously or with a sufficiently small time lag so that the transferable elements of the bioink film have not evolved or migrated spatially in the X, Y and Z dimensions. Known solutions require dissociating the optical analysis phases of the film, and the triggering phases of the shot, or modifying the angle of observation with respect to the direction of the laser.

The temporal or geometric difference between the observation and the laser shot has as an unfavorable consequence in that there is a risk of a change in the state of the transferable bioink film. The laser shot that is then triggered does not reach the aimed target with any certainty.

The known solutions do not allow phase alternation at high frequencies, higher than a few hertz, because it takes significant time after each shot to return the equipment to the observation configuration.

The known solutions do not allow optical analysis to be carried out at the same angle as the laser beam with sufficient resolution to select a specific particle of the bioink film just before the laser shot, nor to simultaneously observe the shot and the development of the transferable bioink film.

In addition, optical assemblies of the prior art create optical aberrations in the observation and focusing area.

Prior art solutions, known as AFA-LIFT, allow combination of a punctual observation of the film area and the focusing of a laser pulse, but not combination of the observation of an extended image of the film area. In the AFA-LIFT solution, the direction of the laser beam is fixed, and it is the film that is movable. The observation is thus limited to a very small field of view corresponding to the area activated by the laser, and, in particular, to a single particle, and does not allow observation of a larger area.

Indeed, the common objective for laser observation and focusing cannot be adapted to the very precise focusing of the laser, and at the same time present an important field of view for observation.

As a result, the previously known solutions do not allow observation of a large area, for example, to automatically select a visible particle in the field, and then control the orientation of the laser beam to activate this selected particle.

The present disclosure also aims to maximize the resolution of the observed image and to avoid any distortion due to a parallax error that occurs when the field of view has a different angle of incidence from that of the laser beam.

BRIEF SUMMARY

The present disclosure concerns a laser-assisted deposition solution based on the direct (absorption of laser radiation) and indirect (creation of a plasma and a cavitation bubble) action of a laser beam to direct the deposition of particles on a printing substrate with micrometric resolution. This process was used to deposit embryonic cells from the spinal cord, guided by laser forces, inside of a fiber, the cells being then expelled one by one from the fiber due to the narrowness of the fiber.

In order to remedy disadvantages of the previously known techniques, the present disclosure concerns, in its most general sense, equipment for depositing particles on a target from a transparent slide carrying a film formed by a fluid containing suspended particles, by local excitation of the film by a laser beam oriented by a controlled optical deflection means, the equipment comprising means for observing the local activation zone by an optical imaging system comprising a sensor and an illumination source whose optical axes are substantially common in the part between an optical splitter and the film, wherein:

(a) the optical beam of the imaging system and the optical beam of the laser are coaxial in the part between the controlled optical deflection means and the film;

(b) the equipment has a first focusing optical unit arranged between the controlled optical deflection means and the film; and c) the equipment has a second image-combining optical unit placed between the sensor and the separator, the sensor being placed in the focal plane of the second optical unit.

For the purposes of the present disclosure, "film" means a thin layer of a substrate, generally liquid or colloidal, containing the particles to be transferred to a target. This layer can have a thickness of a few tens to a few hundreds of micrometers. It can also consist of a layer in a thicker volume of substrate, for example, an intermediate layer of a tank containing the particulate loaded substrate.

For the purposes of the present disclosure, “particle” means an organic, mineral or living particle, in particular:

- nanometric particles such as exosomes or other vesicles produced by cells or nanoparticles of biomaterials (hydroxyapatite) or nanocapsules of biomolecules such as growth factors;
- microscopic particles such as living cells (eukaryotic cells, stem cells, globules, etc.) microparticles of biomaterials and microcapsules of biomolecules; and
- mesoscopic particles such as spheroids made up of clusters of cells or biomaterials.

Preferably, particles are biological particles, including living cells, exosomes and optionally biomaterials.

“Imaging system optical beam” means the light beam emitted from the observed film, between the observed surface of the bioink film and the first optical element, which is usually the scanner ensuring the scanning of the beams, or possibly a collimating lens.

“Laser optical beam” means the light beam emitted by the laser between the surface of the bioink film and the first optical element.

“Substantially common” means that the axis of the imaging beam and the axis of the illumination beam are combined in a reference position of the scanner, for example, the median position. The direction of the imaging beam axis and the illumination beam axis may vary slightly on either side of this reference position, by a value corresponding to the orientation imposed on the observation axis by the scanner, in cases where the illumination axis remains fixed.

Preferably, the optical assembly formed by the first unit and the second unit is configured to have, in the wavelength band of the lighting means, a spatial resolution higher than the spatial resolution of the first unit alone, in the length of the laser.

Advantageously, the resolution $R_T$ of the set formed by the first unit and the second unit is between 1 and 8 μm.

According to a particular variant, the first unit is configured to form a laser spot on the film with a diameter greater than $R_T$.

Advantageously, the first unit is configured to form a laser spot on the film with a diameter of less than 100 μm, and preferably less than 30 μm, with a maximum resolution of a few micrometers.

Alternatively, the laser emits at a wavelength that does not include the visible spectrum, preferably in the infra-red or UV.

Alternatively, the laser emits in a visible light wavelength, and the equipment includes a rejection filter placed on the imaging beam, with a rejection band corresponding to the wavelength of the laser.

According to a particular embodiment, the laser and the light source are activated simultaneously to allow direct observation of the interaction between the laser beam and the film.

According to a particular exemplary embodiment, the film contains living cells.

Preferably, the optical unit consists of a telecentric lens.

According to other embodiments:

- the distance between the film and the optical unit is adjusted to modify the size of the excitation laser spot according to the number of particles to be transferred;
- the optical design of the optical unit and the surface treatments of its constitutive lenses make it possible to prevent any degradation of the optical unit by the energy of the laser beam;
- the focal length ratio of the two optical units makes it possible to form an image in the plane of the camera's sensor such that the smallest observed objects have a size of more than one pixel;
- the three laser, imaging and lighting beams are coaxial and superimposed between the dichroic mirror and the film; and
- the lighting beam is on the other side of the film in a coaxial position but not superimposed with respect to the laser and imaging beams.

The present disclosure also concerns a method for depositing particles on a target from a transparent slide carrying a film formed by a fluid containing suspended particles, by local excitation of the film by a laser beam oriented by a controlled optical deflection means, and imaging the local excitation zone by an optoelectronic imaging system, wherein a succession of images is acquired during a time period surrounding the activation of the laser shot by means of equipment including means for observing the local excitation zone by an optical imaging system including a sensor and a light source whose optical axes are substantially common in the part between an optical splitter and the film, wherein:

(a) the optical beam of the imaging system and the laser beam being coaxial in the part between the controlled optical deflection means and the film;

(b) the equipment having a first focusing optical unit disposed between the controlled optical deflection means and the film; and c) the equipment having a second image-combining optical unit placed between the sensor and the splitter, the sensor being placed in the focal plane of the second optical unit.

BRIEF DESCRIPTION OF THE DRAWINGS

Other characteristics and advantages of embodiments of the present disclosure will appear from the following description, the description being given by way of example only, with reference to the appended drawings in which:

DETAILED DESCRIPTION

Figure 1:
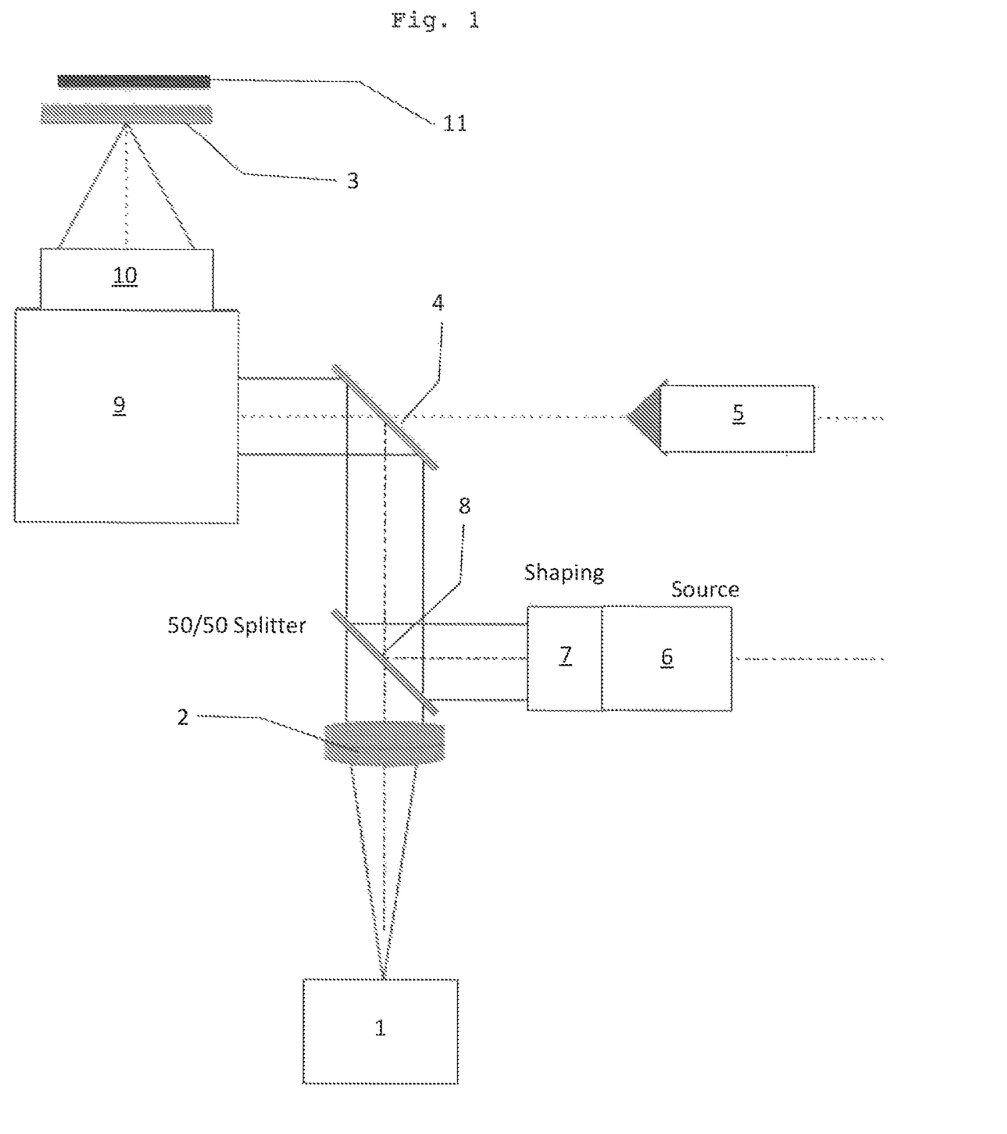
FIG. 1 is a schematic view of a piece of equipment according to a first embodiment of the present disclosure.

FIG. 1 is a schematic view of a first exemplary system in accordance with the present disclosure.

The system includes a camera (1) comprising a high definition sensor, for example, 18 million pixels. For example, the camera (1) is a sensor marketed under the trade name "USB 3 uEye CP" by the IDS company of Obersulm, Germany.

This camera (1) is associated with a second image-combining optical unit (2) acting as a field lens and thus ensuring the conjugation of the image between the focal plane of the film (3) and the plane of the camera sensor (1).

The film (3) is placed in front of a target (11) to which the cells or particles are transferred when a pulsed laser beam (5) is triggered.

For example, the second image-combining optical unit (2) comprises an objective, preferably telecentric, comprising at least two lenses optimized in the visible range.

The optical path is reflected by a high-pass dichroic mirror (4), transmitting the emission wavelength of the laser (5), for example, infra-red, and reflecting the wavelengths in the visible range. This dichroic mirror (4) is oriented so that when it exits, the beam of the imaging system (1), the lighting source (6) and the laser (5) are coaxial and pass through the same focusing path of the first optical unit (10).

The lighting can be diffused, or constituted by a collimated lighting beam. The lighting can be in the visible, or in a band of non-visible wavelengths, for example, infra-red lighting, or ultraviolet lighting for fluorescence excitation. Of course, the imaging system is adapted to the lighting wavelength.

The equipment also includes a light source (6) emitting in the visible range associated with a shaping optics (7) whose function is to collimate the light source (6) if necessary, for example, when the source is divergent from the emitted beam. This lighting source can be a single LED source, a component consisting of an assembly of light-emitting diodes, or a white light source such as incandescent lamps, halogen lamps, supercontinuum laser, etc. The lighting source can also consist of a narrow-spectrum source emitting in wavelengths allowing the excitation of fluorescence of markers or particles.

A separator blade (8) is used to superimpose the lighting optical path and the imaging optical path.

At the exit of the dichroic mirror (4), the two beams heading toward the scanner (lighting and laser) are co-linear with each other and are in fact also co-linear with the imaging beam returning from the film. Thus, the three beams are co-linear between the dichroic mirror (4) and the ink film (3).

The beams are deflected by a scanner (9) ensuring an orientation that is controlled by an external computer.

The scanner (9) provides an angular orientation of the three co-linear beams mentioned above, along two perpendicular axes, two of them being scanned on the film containing the bio-ink, the other being unbalanced into a collimated imaging beam toward the imaging system. The scanner (9) comprises, for example, two mirrors driven by an electromagnetic actuator, for example a scanner marketed by SCANLAB of Puchheim, Germany, under the trade name "SCANcube 14."

The three imaging, lighting and laser beams are thus co-linear and oriented in the same direction at the output of the scanner (9). Thus, the imaging direction and the lighting direction follow the orientation of the laser beam.

The first optical unit (10) has the following functions:
a) to transform the angular orientation into a lateral positioning along two axes X, Y in the plane of the film (3);
b) to focus the laser beam and the lighting beam in the same plane of the film (3); and
c) to collect the light in the visible domain reflected by the film (3), to form the image of the observation area of the film on the sensor of the camera (1).

"Laser beam" means the beam emitted by the laser.

"Imaging beam" means the beam coming from the observation area of the film and directed toward the camera.

The first optical unit (10) comprises a set of lenses forming a telecentric objective with the following characteristics:

In the infra-red spectrum:
  Wavelength: 1030 nm
  Digital opening: >0.10
  Working distance: >10 mm
  Entrance pupil: 12 mm
  Field size: >4 mm
  Damage threshold: >100 J In the visible spectrum:
  Wavelength: 450-600 nm
  Digital opening: >0.10
  Working distance: >10 mm
  Entrance pupil: 12 mm
  Field size: >4 mm In the infra-red spectrum, the lens surfaces are treated with anti-reflective coatings to support high laser energies. This prevents the deterioration over time of the first optical unit (10), the design of which is calculated to prevent the creation of laser "hot spots" within the first optical unit (10).

The dichroic mirror (4) prevents the return of laser infra-red radiation to the camera (1) when a pulse is triggered. Optionally, an infra-red rejection filter can also be placed in the optical path between the dichroic mirror (4) and the camera (1).

The ratio of the focal length of the second optical unit (2) and the focal length of the first optical unit (10) is determined so as to form an image in the plane of the camera sensor (1) such that the smallest observed objects have a size of more than one pixel.

Typically, the resolution $R_T$ of the optical assembly including the second optical unit (2), the camera (1) and the first optical unit (10) is between 1 and 5 µm.

The first optical unit (10) is configured to form a laser spot ("Spot Size or Diffraction Limited") on the film (3) with a cross-section greater than $R_T$ and less than 100 µm.

Figure 2:
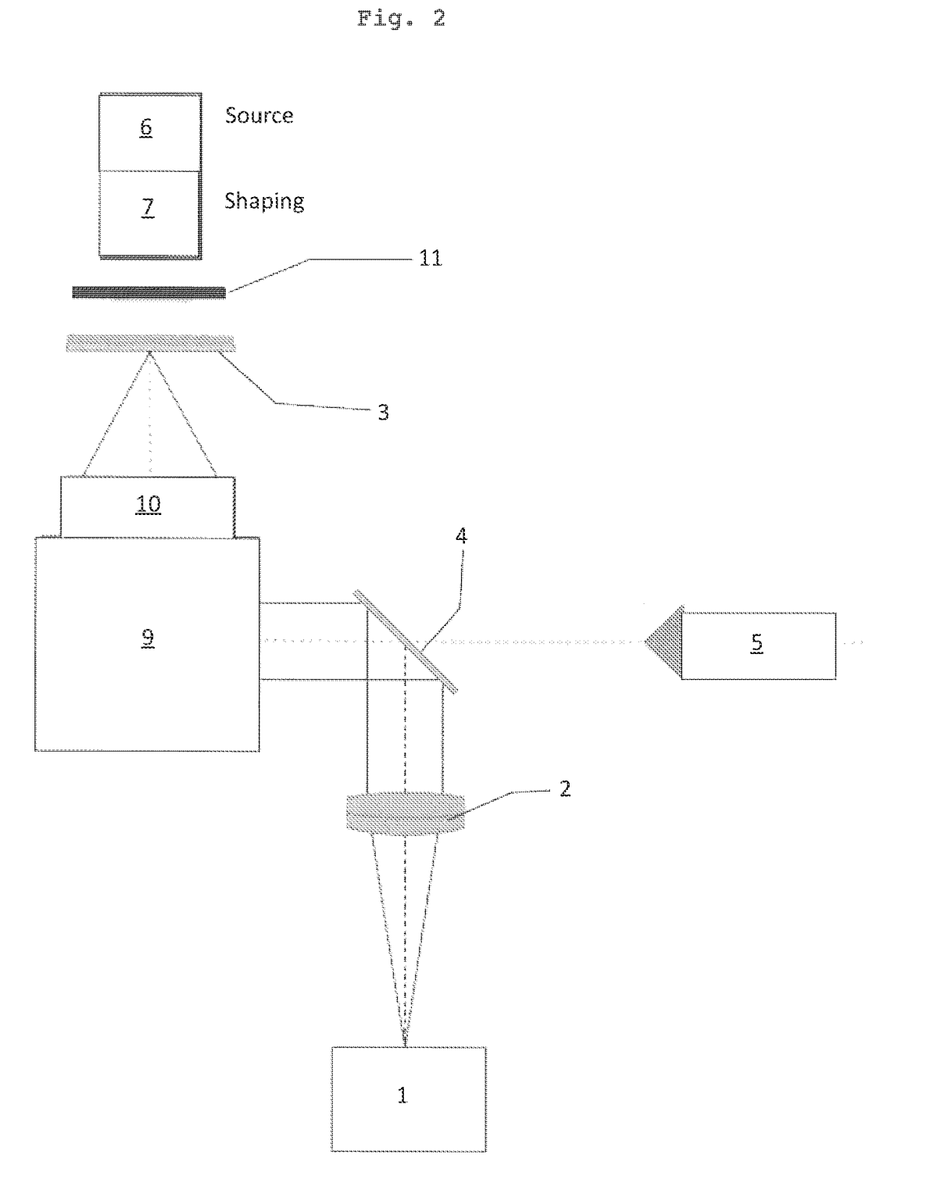
FIG. 2 is a schematic view of a piece of equipment according to a second embodiment of the present disclosure.

FIG. 2 illustrates a different embodiment from the one described above, by the fact that the light source is substantially co-linear with the imaging beam and the laser beam, but arranged on the opposite side of the film (3). This lighting mode allows the observation of a film area in transmission contrast mode, and not in reflection mode as in the first embodiment, which is interesting to improve the detection of particles in certain types of samples. In this configuration, several imaging methodologies can be applied to improve or complete particle analysis, such as:

Transmission microscopy
Dark field microscopy
Insertion of phase slides
Etc.

It also makes it possible to uniformly illuminate the entire viewing area of the film, and to choose the spectral range of the lighting source independently of the optical path between the dichroic mirror (4) and the film (3).

Optionally, the film (3) can be illuminated by both a coaxial beam in the same direction as the imaging beam and the laser beam, and by a second coaxial beam oriented in the opposite direction to the imaging direction.

In this case, the device has no separator blade (8).

The light source (6) is associated with a shaping optics (7) to produce a lighting field covering the entire area scanned by the scanner (9), the direction of the light source being fixed unlike the design of the first embodiment.

This embodiment requires that the substrate of the target (11) be transparent, to allow both illumination in a direction opposite to the laser beam and simultaneous observation.

If the target (11) is opaque, it is necessary to provide a mechanism for moving the target out of the field of observation during the observation phases. In this configuration, observation and laser activation cannot be carried out simultaneously.

Figure 3:
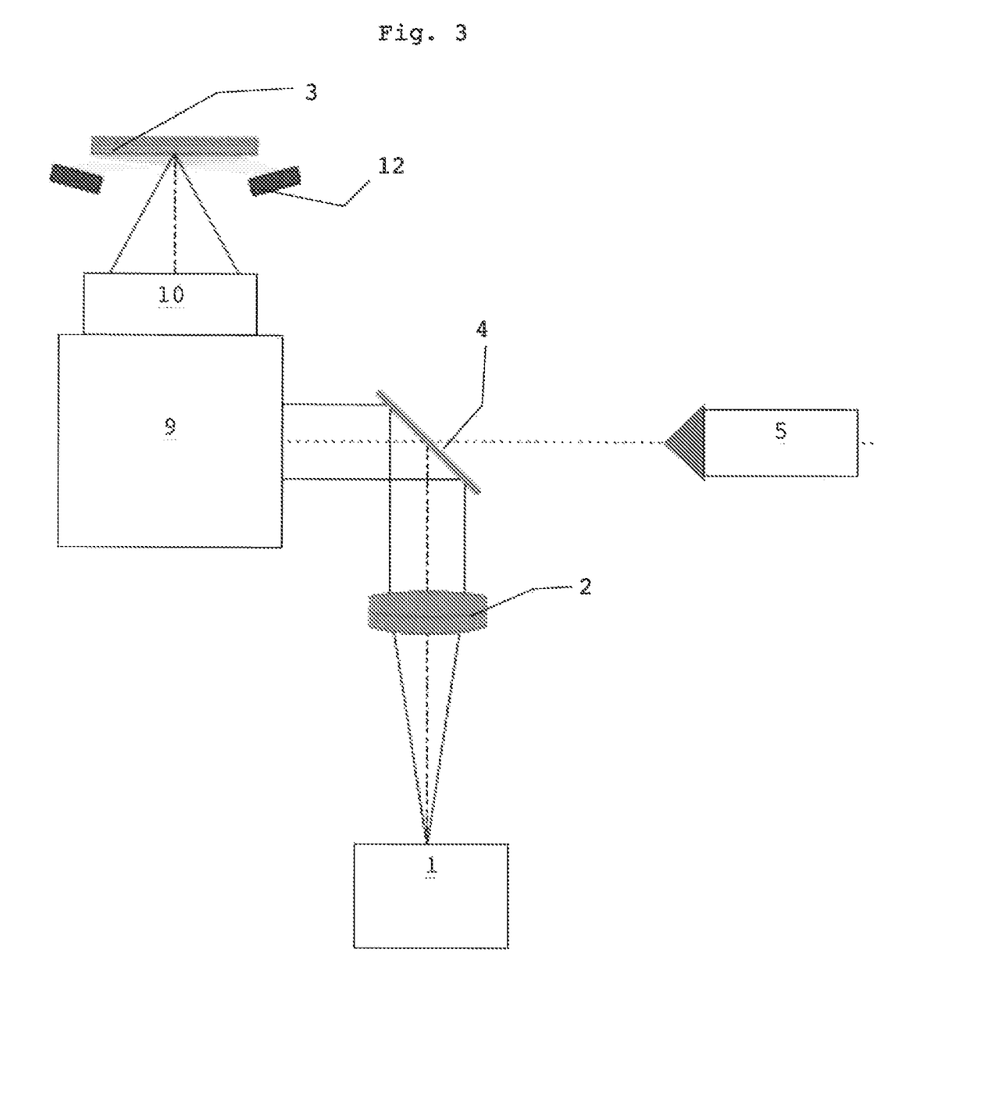
FIG. 3 is a schematic view of a piece of equipment according to a third embodiment of the present disclosure.

FIG. 3 represents another alternative embodiment, in which the lighting is provided by an annular source (12) allowing, in particular, dark field imaging in epi-illumination on opaque objects to be implemented.

This annular source (12) is coaxial with the median axis of the optical unit (10) and produces a fixed light field covering the entire area scanned by the scanner (9).

The source (12) can be placed on the same side as the optical unit (10), with respect to the film (3), or on the opposite side.

The annular source (12) also makes it possible to uniformly illuminate the entire viewing area of the film, and to choose the spectral range of the illumination source independently from the optical path between the dichroic mirror (4) and the film (3).

Figure 4:
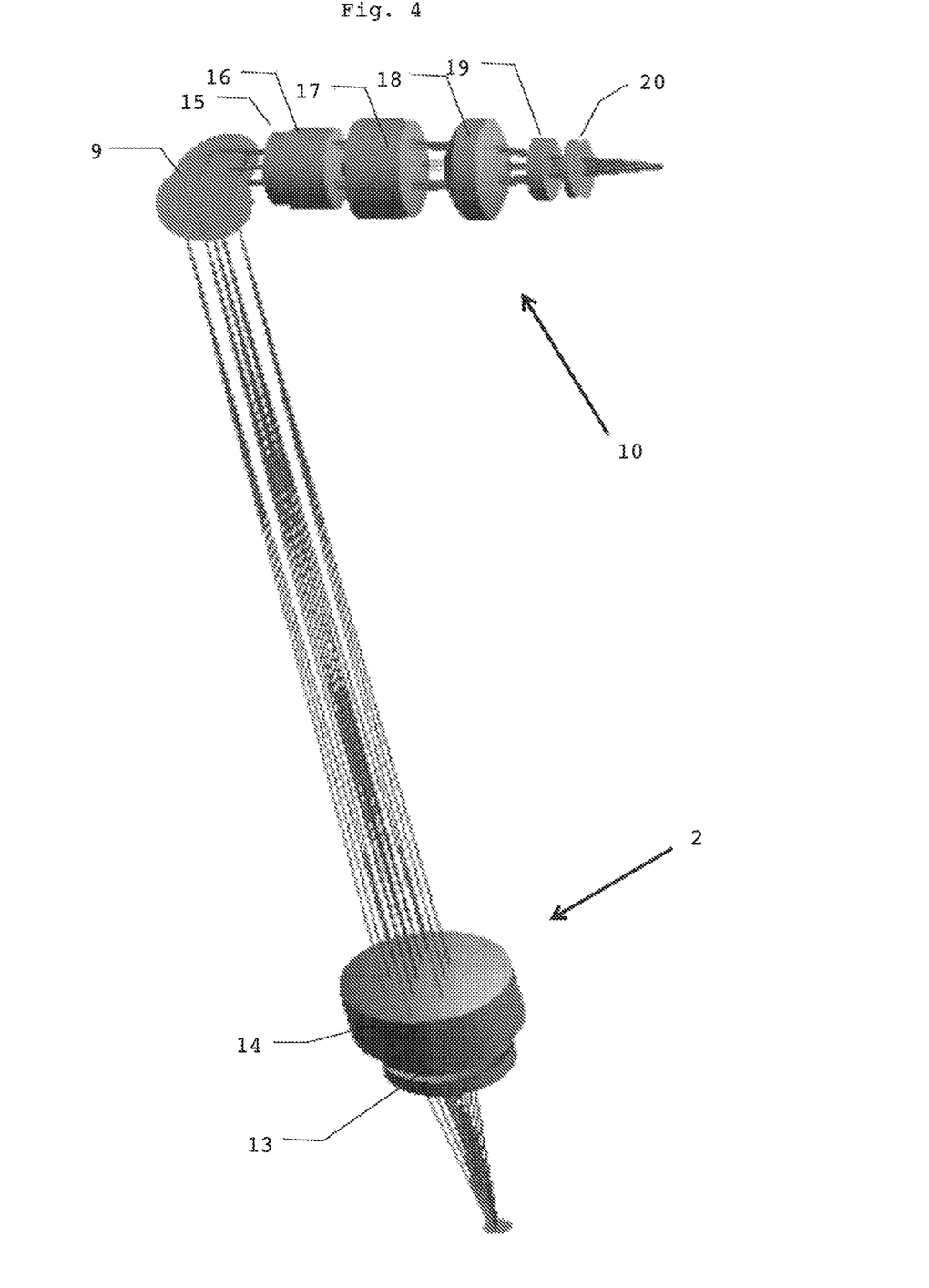
FIG. 4 shows a detailed schematic view of the optical diagram of the lens and the second image-combining optical unit.

FIG. 4 shows a detailed view of the optical diagram corresponding to the first embodiment.

The second optical unit (2) consists of a first and second lens (13, 14).

The first lens (13), on the camera (1) side, consists of a convex lens.

The second lens (14) consists of a doublet formed by a convex-concave lens and a convex lens with a large focal length, corresponding substantially to the length of the optical path, typically more than 100 mm.

The optical unit (10) consists of an assembly of six lenses, with three convex-concave input lenses (15 to 17) and three convex output lenses (18 to 20).

The optical designs described herein for each optical unit (2) and (10) are given only as an example of an embodiment that fully meets the specifications described in the first embodiment. The number of lenses, their characteristics and positioning could be different while achieving the desired performance. Characteristics such as cost, integration complexity, lifetime, have a direct impact on the design chosen according to the intended application.

Figure 5:
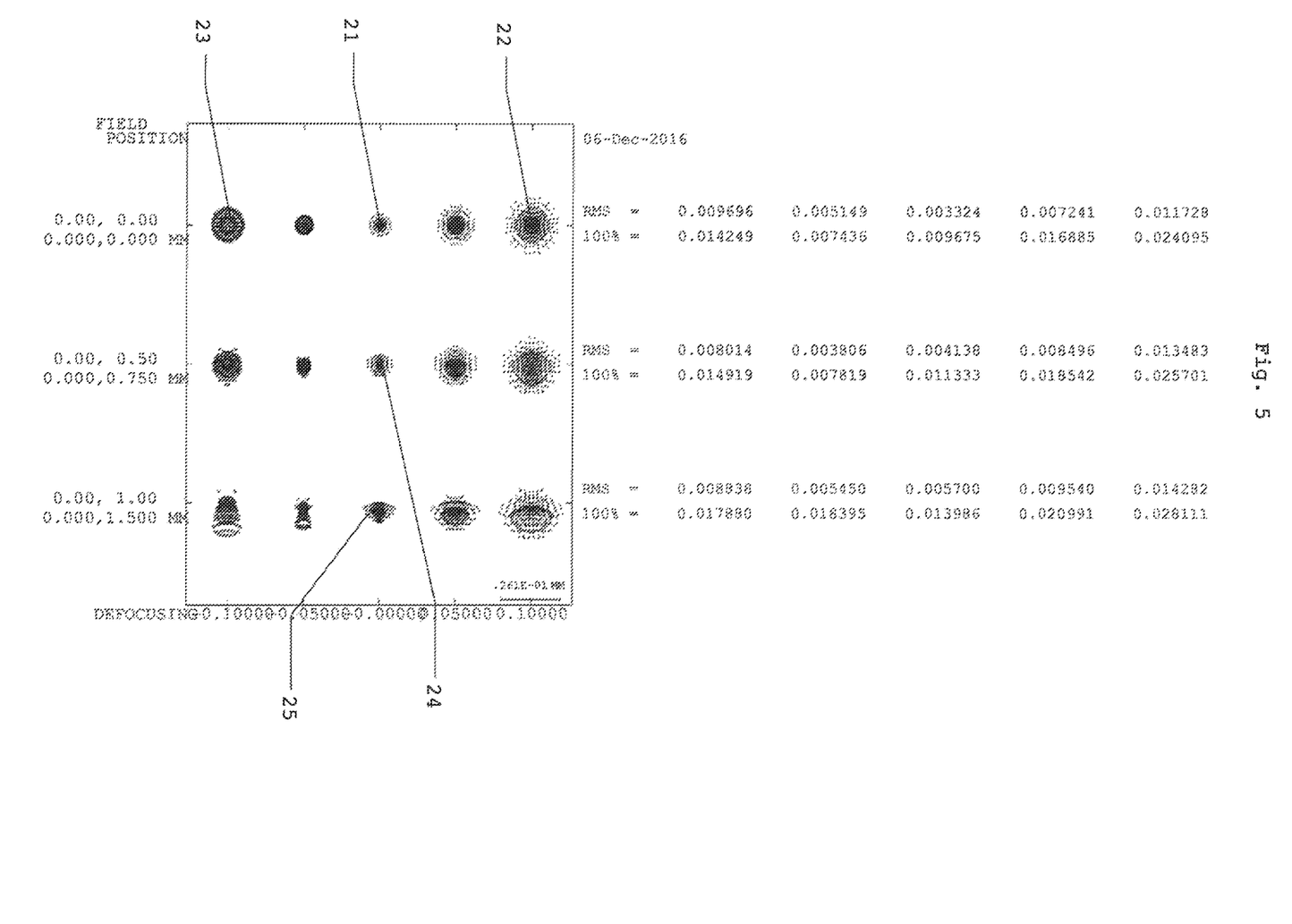
FIG. 5 shows an exemplary spot diagram.

FIG. 5 shows an example of the shape of the laser spot, for different orientations controlled by the scanner (9) and for different positions of the film (3) with respect to the focal plane of the optical unit (10).

It should be noted that the plane of the film (3) is not necessarily confused with the focal plane of the optical unit (10), but can be shifted to:

modify the section and shape of the laser spot; and
separate the imaging plane from the laser plane to observe a plane at a higher or lower level than the laser focusing plane.

For this purpose, the equipment may have means to control a displacement of the relative distance between the film (3) and the optical unit (10) in a direction perpendicular to the planes. The effect is to adjust the spot size and to cover one or more particles, depending on the number of cells or particles to be transferred to the target (11).

The spot (21) corresponds to a situation where the focal plane and the film (3) are combined, and the spot is in the center of the field scanned by the laser (5). In this situation, the spot (21) has a minimum cross-section, in the described example 3.3 micrometers, with minimum aberrations. The intensity of the spot is highest in this central area of the field.

When the two planes are offset, there is an enlargement of the spot as illustrated by the spot (22) where the cross-section is 11.7 micrometers. This situation allows transfer of several particles arranged in the area covered by this spot. The same situation is observed with the spot (23) corresponding to a shift of the two planes in the opposite direction.

When the angular orientation fixed by the scanner (9) is deviated from a median orientation, there is a slight widening of the spot as illustrated by the spots (24) and (25), corresponding to orientations on opposing sides of the median direction.

The use of a telecentric lens has the effect of limiting variations in spot size due to optical aberrations, which remain lower than the enlargements observed in the event of a plane shift. It also makes it possible not to pull obliquely with respect to the imaged surface as conventional lenses do, thus guaranteeing a much more homogeneous and reproducible image quality in the field.

Figure 6:
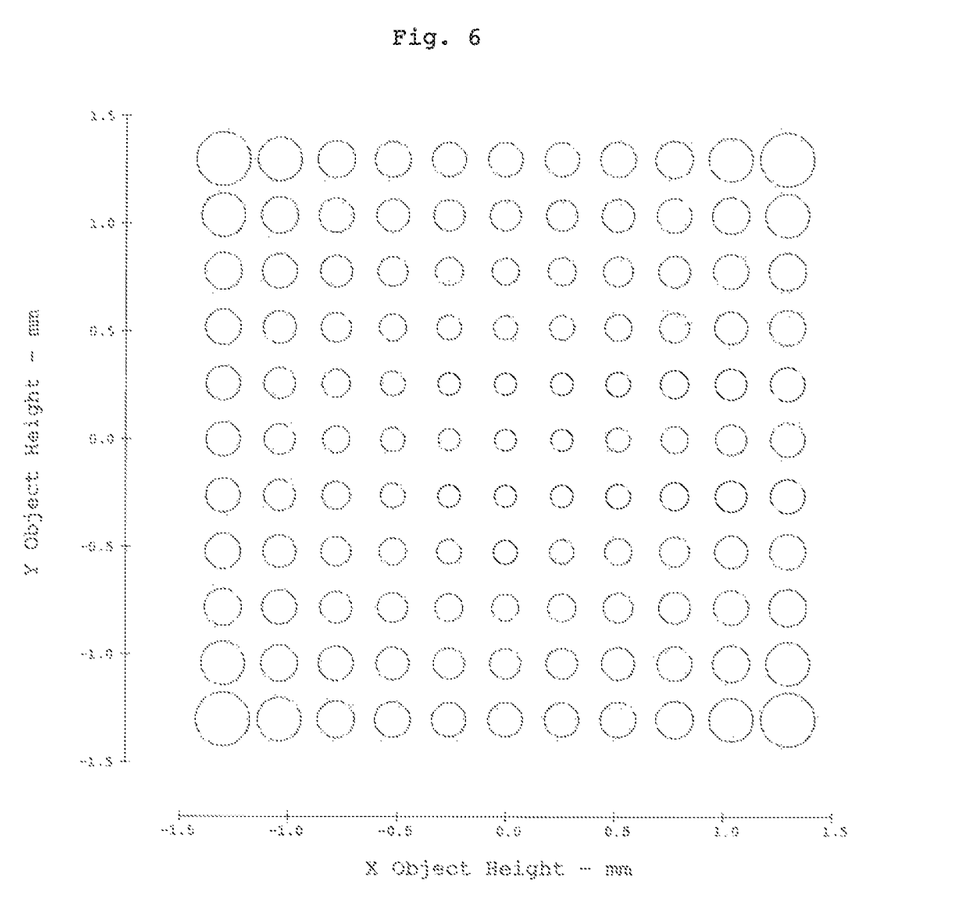
FIG. 6 shows a front view of the optical distortions of the observed field.

FIG. 6 illustrates the variation, when the focal plane of the optical unit (10) is coplanar with the plane of the film (3), of the size of the spots on the surface scanned by the scanner (9) for the optical design described in the section "3D Representation of the optical design." This performance could be significantly different for another optical design.

A fairly good dimensional constant is observed over the entire field of 3 millimeters by 3 millimeters, which allows a particle to be selected over the entire observed area without significantly degrading the efficiency of the transfer.

For example, the spot cross-section varies between 3.3 and 8 micrometers depending on the position in the field, with an average of 5 micrometers.

Since the laser beam is co-linear with the lighting beam and the imaging return beam, the imaging and laser pulses areas are totally superimposed and linked to the movement/position of the scanner.

The sequence is as follows:

the scanner is positioned with respect to a particular area of the transfer film and the light beam illuminates an area of a few square millimeters in order to generate the image of the film. Generally, this area contains several transferable particles, which can be selected by controlling the scanner before the laser shooting sequence;

the return imaging beam follows the opposite path to the sensor that acquires the image of the film area;

then, a computer processing enables:
- rebuilding the image;
- correcting the image to make it more easily usable (noise suppression, removing biases, etc.); and
- process the image using mathematical algorithms to analyze its main components, namely particle detection and position mapping; and from the positions of the particles, a trajectory of laser shots is calculated enabling matching of the laser shots (and, therefore, the number of particles to be printed) with the desired printing pattern (from the CAD of the object to be printed).

The collinearity of the imaging and shooting, ensured by the single lens, allows the printing process to be monitored at any time and adapted according to the natural (environment) or induced (laser shooting) movements of the film. Thus, the printing pattern is optimized in real time to obtain a maximum correlation between the calculated printing file (upstream) and the actual printing, each laser shot corresponding to a known quantity of particles or particles to be deposited.

Optionally, the imaging system also allows the target to be observed and the process of particle deposition on the target to be monitored. In this case, the focus of the optical system is modified to observe the working area and the target alternately.

Another solution is to provide a second imaging system for target observation. This second imaging system is capable of observing the target in a direction opposite to the direction of the laser beam, when the target is transparent, or in the same direction, with a sequential switch-over of the imaging systems.

The invention claimed is:

1. A system for depositing particles on a target, comprising:
    a transparent slide for supporting a fluid film containing the particles in suspension;
    a laser configured to emit a laser beam onto a localized area of the fluid film;
    a deflection device configured to selectively deflect the laser beam onto selected localized areas of the fluid film;
    an imaging system configured to acquire images of the localized areas of the fluid film, the imaging system including a sensor and a light source, an optical axis of the sensor and an optical axis of the light source being at least substantially aligned with one another in a region between an optical splitter and the fluid film;
    a first focusing optical unit disposed between the deflection device and the fluid film; and
    a second image-combining optical unit disposed between the sensor of the imaging system and the optical splitter, the sensor being located in a focal plane of the second image-combining optical unit; and
    wherein an optical beam of the imaging system and an optical beam of the laser are coaxial in a region between the deflection device and the fluid film.

2. The system of claim 1, wherein a resolution of an optical assembly formed by the first focusing optical unit and the second image-combining optical unit in a wavelength band of light emitted by the light source is higher than a resolution of the first focusing optical unit alone in a wavelength of the laser beam.

3. The system of claim 1, wherein a resolution of an optical assembly formed by the first unit and the second unit is between 1 μm and 8 μm.

4. The system of claim 1, wherein the first optical unit is configured to form a laser spot on the fluid film, the laser spot having a diameter greater than a resolution of an optical assembly formed by the first unit and the second unit.

5. The system of claim 4, wherein the laser spot has a diameter of less than 100 μm.

6. The system of claim 1, wherein the laser beam does not include wavelengths in the visible region of the electromagnetic spectrum.

7. The system of claim 1, wherein the laser beam emits wavelengths in the visible region of the electromagnetic spectrum, the system further comprising a rejection filter placed in an optical path of the imaging system, the rejection filter having a rejection band corresponding to the wavelengths of the laser beam.

8. The system of claim 1, wherein the laser and the light source are capable of being activated simultaneously to allow observation of interaction between the laser beam and the fluid film.

9. The system of claim 1, further comprising a fluid film containing living cells on the transparent slide.

10. The system of claim 1, wherein the first optical unit comprises a telecentric lens.

11. The system of claim 1, further comprising a device for adjusting a distance between the fluid film and the first optical unit to modify a size of the localized area of the fluid film onto which the laser beam is directed.

12. The system of claim 1, wherein a focal length ratio of the first optical unit and the second image-combining optical unit allows an image to be formed in the focal plane of the imagining system such that the smallest objects observed by the sensor have a size of more than one pixel of the sensor.

13. The system of claim 1, wherein optical paths of each of the laser, the light source, and the sensor are coaxial and superimposed between a dichroic mirror and the fluid film.

14. The system of claim 1, wherein a light beam emitted by the light source is directed onto the fluid film from a side of the fluid film opposite to a side of the fluid film onto which the laser beam is directed, the light beam and the laser beam being coaxial.

15. A method for depositing particles on a target, comprising:
    providing a fluid film containing suspended particles on a surface of a transparent slide located proximate to the target;
    locally exciting a region of the fluid film using a laser beam while controlling an orientation of the laser beam using a controllable optical deflection device; and
    imaging the locally excited region of the fluid film using an imaging system, the imaging comprising acquiring a succession of images during a time period surrounding an activation of a pulse of the laser beam, the imaging system comprising a sensor and a light source, an optical axis of the sensor and an optical axis of the light source being at least substantially aligned with one another in a region between an optical splitter and the fluid film; and
    wherein an optical beam of the imaging system and the laser beam are coaxial in a region between the controllable optical deflection device and the fluid film, a focusing first optical unit is disposed between the controllable optical deflection device and the fluid film, and an image-combining second optical unit is disposed between the sensor and the optical splitter, the sensor being disposed in a focal plane of the image-combining second optical unit.

16. The method of claim 15, wherein a resolution of an optical assembly formed by the first unit and the second unit in a wavelength band of light emitted by the light source is higher than a resolution of the first optical unit alone in a wavelength of the laser beam.

17. The method of claim 15, wherein a resolution of an optical assembly formed by the first unit and the second unit is between 1 μm and 8 μm.

18. The method of claim 15, wherein the first optical unit is configured to form a laser spot on the fluid film, the laser spot having a diameter greater than a resolution of an optical assembly formed by the first unit and the second unit.

19. The method of claim 18, wherein the laser spot has a diameter of less than 100 μm.

20. The method of claim 15, further comprising simultaneously activating the laser beam and the light source and acquiring at least one image illustrating interaction between the laser beam and the fluid film.

\* \* \* \* \*